United States Patent [19]
Pohndorf et al.

[11] Patent Number: 5,353,800
[45] Date of Patent: Oct. 11, 1994

[54] IMPLANTABLE PRESSURE SENSOR LEAD

[75] Inventors: Peter J. Pohndorf, Stillwater; Peter M. Mulier, St. Paul, both of Minn.

[73] Assignee: Medtronic, Inc., Minneapolis, Minn.

[21] Appl. No.: 989,298

[22] Filed: Dec. 11, 1992

[51] Int. Cl.$^5$ ............................................. A61B 5/00
[52] U.S. Cl. ................... 128/673; 128/748; 128/675
[58] Field of Search ............... 128/673, 675, 748, 642, 128/785; 73/756, 754, 723–728; 607/129, 130, 131

[56] References Cited

U.S. PATENT DOCUMENTS

| | | |
|---|---|---|
| 3,473,386 | 12/1967 | Nielson et al. . |
| 4,023,562 | 5/1977 | Hynecek et al. . |
| 4,281,667 | 8/1981 | Cosman ................. 128/748 |
| 4,407,296 | 10/1983 | Anderson et al. . |
| 4,485,813 | 12/1984 | Anderson et al. . |
| 4,774,950 | 10/1988 | Cohen . |
| 4,817,629 | 4/1989 | Davis et al. ............. 128/675 |
| 4,846,191 | 7/1989 | Brockway et al. ........ 128/673 |
| 4,899,751 | 2/1990 | Cohen . |
| 4,899,752 | 2/1990 | Cohen . |
| 4,936,304 | 6/1990 | Kresh et al. . |
| 4,944,724 | 7/1990 | Goldberg et al. ........ 128/673 |
| 4,967,755 | 11/1990 | Pohndorf . |
| 4,986,270 | 1/1991 | Cohen . |
| 4,998,977 | 3/1991 | Preiss et al. ........... 128/673 |
| 5,027,816 | 7/1991 | Cohen . |

Primary Examiner—Kyle L. Howell
Assistant Examiner—Robert L. Nasser, Jr.
Attorney, Agent, or Firm—Reed A. Duthler; Harold R. Patton

[57] ABSTRACT

A pressure sensing lead, wherein a hollow needle extending from the distal end of the lead is coupled to a pressure transducer. The hollow needle may be coiled and adapted to be screwed into human tissue, for example through the ventricular septum from the right ventricle into the left ventricle of a patient's heart, or through the wall of the heart into the pericardial sac. Alternatively, the hollow needle may be straight and a separate coiled needle mounted around the straight needle may be provided to affix the lead to body tissue. Pressure gradients are communicated from the tip of the hollow needle to its base and applied to the pressure sensor, allowing, for example, left ventricular pressure measurements to be taken from the right ventricle or pericardial sac pressure measurements to be taken from within the heart without the necessity of the pressure sensor itself passing through the heart wall.

17 Claims, 5 Drawing Sheets

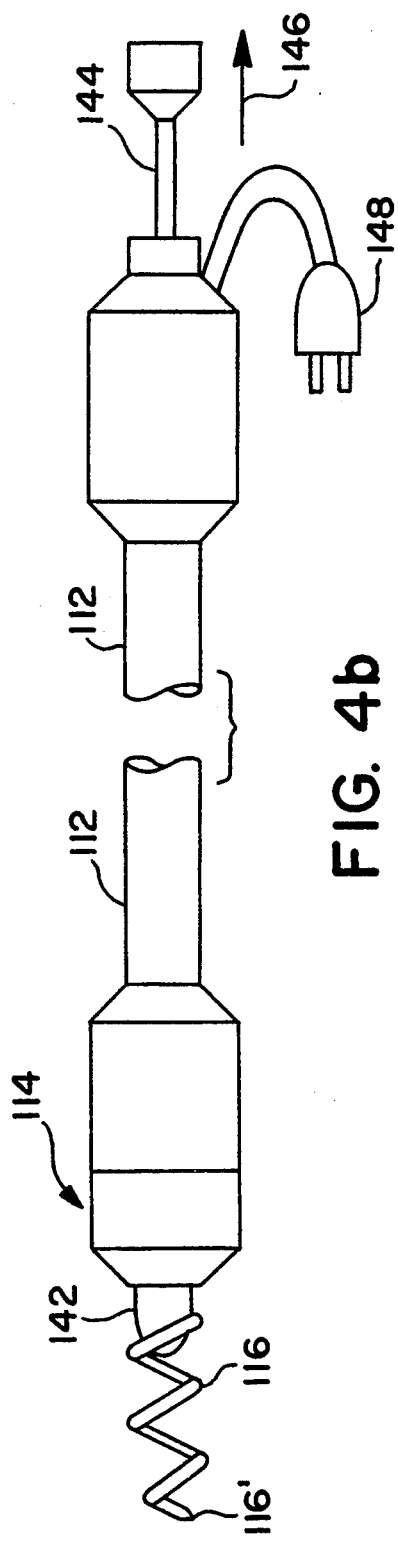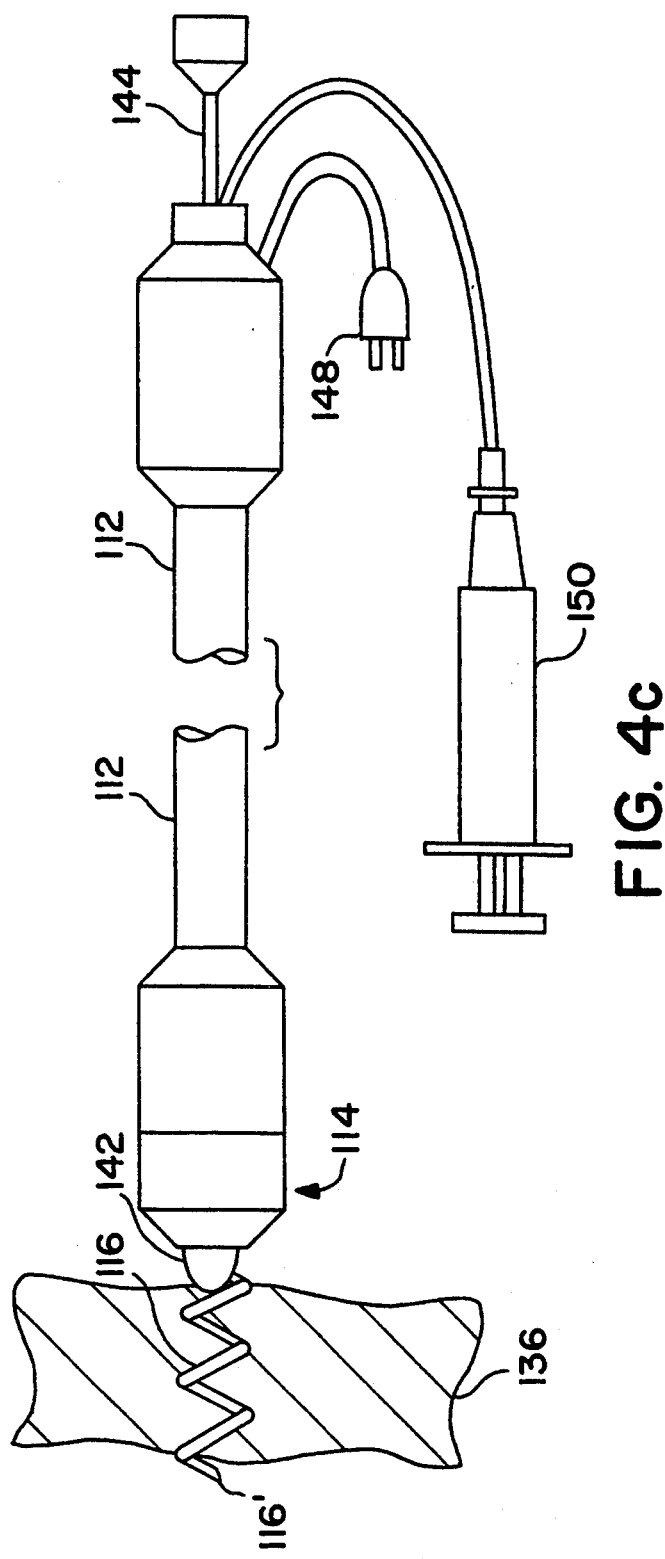
FIG. 4b
FIG. 4c

IMPLANTABLE PRESSURE SENSOR LEAD

BACKGROUND OF THE INVENTION

This invention relates to the field of implantable medical devices, and more particularly relates to an implantable pressure sensing lead.

Pacemakers are available which are capable of varying their pacing rates in response a patient's metabolic need for cardiac output. Some such rate-responsive or rate-adaptive pacemakers utilize physiologically-based signals, such as signals from sensors for measuring the pressure inside the patient's right ventricle, intramyocardial pressure, myocardial contractility to derive a measurement of demand for cardiac output.

Sensing pressure at certain sites within the patient's body offers potential for accurate determination of a patient's metabolic needs. One of the earlier successful methods of pressure measurement was through the use of a catheter, as described in U.S. Pat. No. 3,473,386 to Neilsen et al. A disadvantage of the catheter approach, however, lies in its lack of accuracy. An implantable pressure sensor is described in U.S. Pat. No. 4,023,562 to Hynecek et al.; however, the Hynecek et al. sensor is not suitable for chronic implantation, as body fluids destroy the pressure transducer in a relatively short time.

In U.S. Pat. No. 4,936304 to Kresh et al. there is proposed a pressure sensor arrangement for controlling pacemaker function by detecting changes in the contractile state of the cardiac muscle. The Kresh et al. '304 patent suggests that a pressure sensor within the threaded distal end of a transvenous lead may be partially embedded in the myocardium, so that forces exerted on the distal end of the lead resulting from myocardial contraction may be detected. The Kresh patent contemplates introduction of a pressure sensor into the cardiac muscle at the apex of the right ventricle, in order to obtain readings correlated to intramyocardial contractility. However, the patent states that introduction of the pressure sensor into the ventricular wall is not preferable for providing a good indication of wall stress changes resulting from changing contractility, due to the thinness of the right ventricular wall.

In U.S. Pat. No. 4,407,296 to Anderson there is described a chronically implantable pressure sensor suitable for use in conjunction with a long-term implantable device such as a pacemaker. Other examples of chronically implantable pressure sensors are described in U.S. Pat. No. 4,485,813 to Anderson et al. and in U.S. Pat. No. 4,432,372 to Monroe. In the types of pressure sensing arrangements proposed in these patents, the pressure sensors must be hermetically sealed to allow chronic implantation. This tends to increase the size of the pressure sensors. Also, since the pressure sensors of the prior art are typically disposed on a lead, they may only be located in places accessible through conventional lead implantation techniques. The above-referenced Anderson '296, Anderson et al. '813, and Monroe '372 patents, for example, contemplate disposing the pressure sensor in the right ventricle of a patient, so that right-ventricular pressure readings, or right-ventricular muscle motion readings, are available.

U.S. Pat. Nos. 4,774,950, 4,899,751, 4,899,752, 4,986,270, and 5,027,816 to Cohen each contemplate locating a pressure sensor at various sites in the circulatory system, including the right atrium, the right ventricle, the left atrium, the left ventricle, or in a major artery. However, particularly in the case of the left-atrial, left-ventricular, and other arterial sites, the above-noted Cohen patents do not address the issue of how a pressure sensor may be reliably introduced into those sites in any substantial detail or address the specific construction of sensors for long term implant in such locations.

Notwithstanding the sensors described in the prior art discussed above, there continues to be room for improvement in the area of assessing a patient's metabolic need particularly for controlling pacemaker rate. In particular, there remains a need for practical pressure sensors for chronic measurement of pressure within the heart tissue, within the left ventricular cavity and elsewhere that conventional pressure sensing leads cannot readily be placed by means of the transvenous introduction of a sensor lead into the right heart.

SUMMARY OF THE INVENTION

The present invention, therefore, relates to a pressure sensing apparatus suitable for chronically assessing proper functioning of a patient's heart, for assessing proper operation of an implantable therapeutic device, and/or for enabling an implantable therapeutic device, such as a pacemaker, cardioverter, or defibrillator, to adapt itself to the continually changing metabolic needs of the patient.

In the present invention, a hollow needle is utilized to communicate pressure to a pressure transducer. The needle/transducer combination may be disposed at the distal end of a transvenous lead, so that the sensor signals reflecting pressure communicated through the needle may be applied to suitable sensor circuitry, in an implantable device. This feature allows pressure sensing in locations inappropriate for direct implantation of the sensor itself. In other embodiments the pressure communicating needle is adapted to be coupled to a pressure sensor located external to the lead. A fixation helix, adapted to be screwed into heart tissue is also provided, to anchor the distal end of the lead in place. In some embodiments the fixation helix and the pressure communicating needle are combined into a single element taking the form of a hollow, helical needle.

In using the invention, the pressure-communicating needle may be located with the its distal end either partially or completely puncturing the cardiac muscle. Thus, the needle tip can be disposed, for example, in a patient's left ventricle, in the pericardial sac surrounding the heart or in the heart muscle itself. In this way, left ventricular pressure readings, intramyocardial and pericardial sac pressure readings are made available to the implanted device.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein:

FIGS. 4a, 4b, and 4c are illustrations of a lead and pressure sensor assembly in accordance with an alternative embodiment of the present invention;

DETAILED DESCRIPTION OF SPECIFIC EMBODIMENTS OF THE INVENTION

Figure 1:
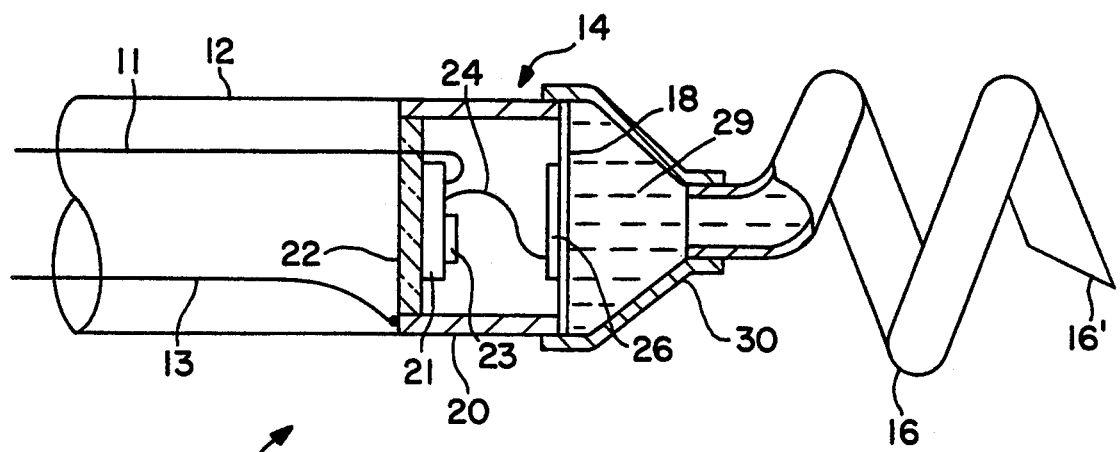
FIG. 1 is a partially cut-away view of a lead and pressure sensor assembly in accordance with one embodiment of the invention.

FIG. 1 is a partially cut-away view of a pressure sensor and hollow needle assembly 10 in accordance with one embodiment of the present invention. Sensor/needle assembly 10 is disposed at the distal end of a conventional implantable lead 12 having at least two mutually insulated conductors 11, 13 therein, for carrying electrical signals between transducer 14 and circuitry in a medical device (not shown) either implanted or external to the patient.

Sensor/needle assembly 10 comprises a pressure sensor 14 coupled to sense pressure changes within the annular volume defined within a hollow, coiled needle 16. In the presently preferred embodiment of the invention, it is contemplated that any one of various known types of pressure sensors would be suitable for the purposes of practicing the invention. Sensor 14 may optionally correspond to any of the pressure sensors disclosed in U.S. Pat. No. 4,485,813 to Anderson et al, U.S. Pat. No. 4,967,755, issued to Pohndorf, or U.S. Pat. No. 4,407,296 all of which are incorporated herein by reference in their entireties.

In the illustrated embodiment the pressure sensor corresponds generally to that disclosed in the above-cited Pohndorf case. A thin metallic membrane 18 positioned across a front portion of a metal housing 20 to form a diaphragm. The rear portion of housing 20 is plugged with a feedthrough assembly 22 through which conductor 11 passes. Hybrid substrate 21 carries an FET 23 and associated protection diodes. A wire 24 connects the gate terminal of FET 23 to one side of piezoelectric crystal 26 which is bonded to diaphragm membrane 18 so that movement of diaphragm membrane 18 causes crystal 26 to flex. The other side of crystal 26 is electrically coupled to the diaphragm 18 and thereby to housing 20. Conductor 11 is coupled to the source terminal of FET 23. Conductor 13 is coupled to the housing 20, which in turn is coupled to the drain terminal of FET 23.

To activate the pressure sensor, the device to which the sensor is coupled applies an electrical power signal to the conductors 11 and 13. Diaphragm deflections result from pressure being applied to the outer surface of diaphragm membrane 18. Crystal 26 acts as a high-impedance voltage source in response to diaphragm deflections, which voltage is used to modulate current flow through the FET and thus provide a signal indicative of the deflections of the crystal 26. In the event that the device to which the lead is connected is a cardiac pacer, needle 16 may be electrically conductive, conductor 13 may also be coupled to the sense amplifier and to the output circuitry of the pacer so that needle 16 may act as a cardiac pacing and sensing electrode.

Hollow needle 16 is disposed so that the annular volume within the needle communicates with diaphragm membrane 18 such that pressure gradients at tip 16' of needle 16 are communicated through the annular volume of needle 16 to cause deflections of diaphragm membrane 18. As shown in FIG. 1, a funnel-shaped adapter element 30 may be employed to couple the base of needle 16 to the conductive housing 20 of sensor 14 which in turn is coupled to conductor 13.

Several design alternatives have been contemplated by the inventors with respect to the configuration of hollow needle 16. As sensor assembly 10 is intended to be implanted in a patient, it is of course desirable that it not be allowed to introduce air into the patient's circulatory system, since this could lead to serious embolic complications. If needle 16 is indeed entirely hollow, some provision may be made, such as by means of a lumen within lead 12, for drawing blood into needle 16 as by back-flow, at the time the assembly is introduced into the patient. Alternatively, needle 16 and funnel 30 may be filled with a pressure-conducting medium 29, such as fluid silicone or saline, contained at tip 16' of needle 16 by means of a flexible membrane, and in communication with sensor membrane 18 at the base of needle 16. As a further alternative, needle 16 and funnel 30 may be filled with a resilient material like silicone rubber.

Figure 2:
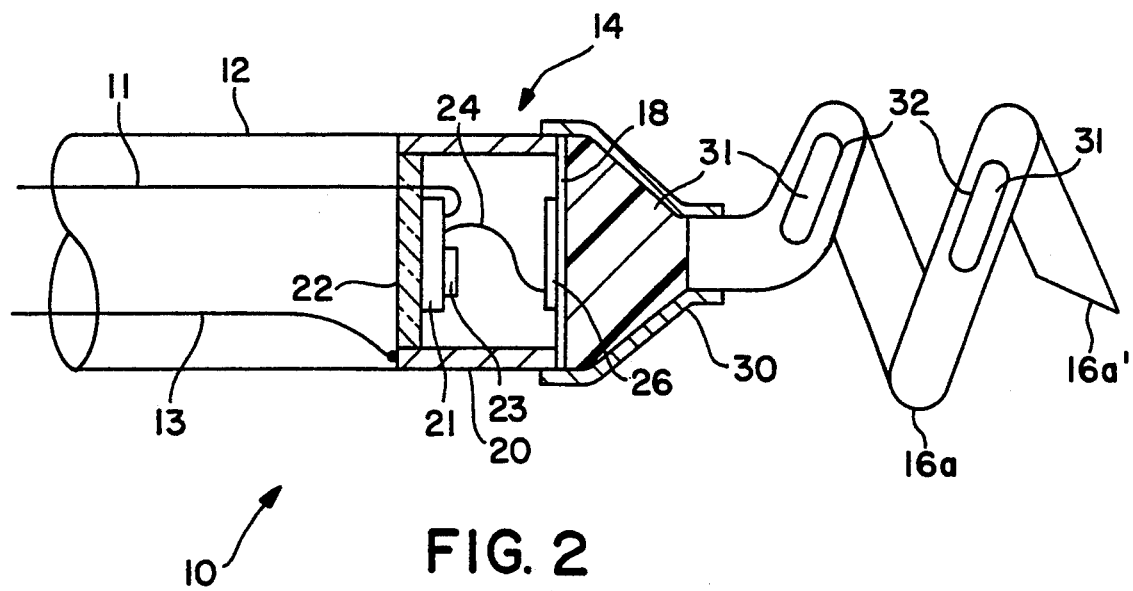
FIG. 2 is a partially cut-away view of the lead and pressure sensor assembly of FIG. 1 as modified.

In FIG. 2, an alternative embodiment including a modified hollow coiled screw 16a is shown. All other components shown are identical to, and retain identical reference numbers as those of FIG. 1. Modified screw 16a is provided with a plurality of openings or ports 32 along its coiled length, these ports 32 providing additional opportunity for pressure gradients to be communicated through the annular volume of needle 16 to sensor 14. In this embodiment, hollow needle 16a is filled with silicone rubber 31 or some other pressure-conducting biocompatible material as previously described with reference to the embodiment of FIG. 1. It is contemplated that holes 32 may be formed in needle 16a by means of known laser cutting techniques or the like.

A frequency filtering effect upon pressure gradients communicated through needle 16 has been observed. Ideally, of course, it would be preferable for sensor/needle assembly 10 to have a flat frequency response from at least zero to one-hundred hertz. However, for practical purposes, it is contemplated by the inventors that a flat frequency response in the range between zero and approximately twenty hertz is acceptable. The inventors' experimental results have shown that such a response can be achieved with a twenty-two gauge needle having a length of about one inch.

Figure 3:
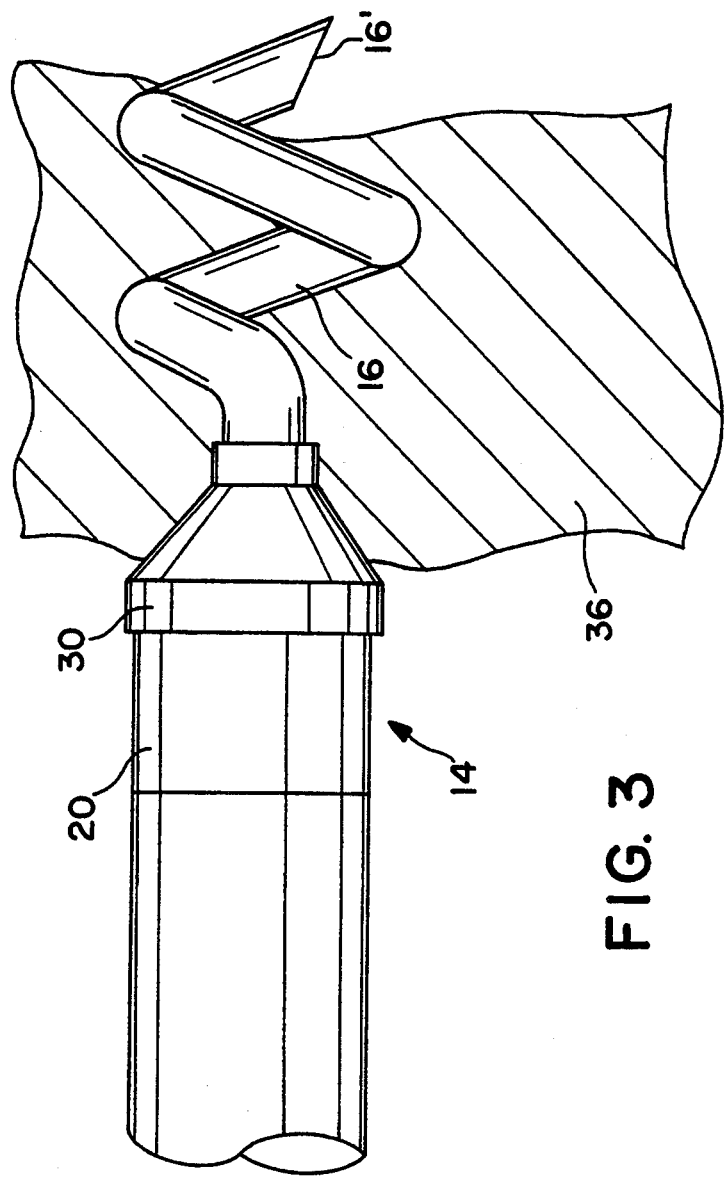
FIG. 3 is an illustration of the lead and sensor assembly from FIG. 1 as implanted.

Operation of sensor/needle assembly 10 (FIG. 1) is illustrated in FIG. 3. In Sensor/needle assembly 10 is shown with needle portion 16 having been screwed into myocardial tissue 36, which may be the ventricular septum of a patient's heart. In this case, pressure readings provided from sensor 14 will substantially correlate to the left ventricular pressure, and will therefore provide an indication of proper functioning of the heart as blood is pumped through the patient's circulatory system. Such information may be useful in several ways, such as providing an indication of congestive heart failure.

Alternatively, tissue 36 may be the right-ventricular wall right atrial wall of a patient. In this case, i.e., when needle tip 16' is exposed in the pericardial sac, pressure readings from sensor 14 will reflect pressure exerted not only from the contractions of the heart, but also pressure exerted by expansion and contraction of the patient's lungs. These pressure readings can provide an excellent indication of the patient's respiratory rate, information which is useful as a basis for controlling the stimulation rate of a rate-adaptive pacemaker, for example.

Lead 12 may be transvenously introduced into a patient's right ventricle or atrium by conventional means, i.e., by any of the known techniques used for introducing screw-in leads that are often used in conjunction with cardiac pacemakers. The depth of penetration of needle tip 16' into myocardial tissue 36 is substantially related to the number of times needle 16 is turned during the introduction and placement procedure.

While the transmural or trans-septal disposition of needle 16 described above with reference to FIG. 3 might be expected by those of ordinary skill in the art to be undesirable due to the risk of such complications as tamponade, and the like, the inventors' experimental experience has been quite to the contrary; the inventors' have found that the heart muscle tends to seal around the needle as the muscle contracts. One reason for this is that the puncture caused by needle 16 is extremely small; the inventors believe that such would not be the case if a trans-septal or transmural puncture large enough to allow introduction of sensor 14 itself were made.

In the case of a transmural implant of assembly 10, verification that the needle has punctured the myocardial wall can be verified electrically, either through measurement of electrical impedance or through measurement of pacing threshold. The inventors have found that upon complete penetration of the myocardial wall by needle 16, the patient's pacing threshold increases dramatically, i.e., on the order of 30% or so, and that the pacing impedance changes even more dramatically, i.e., by as much as 70%. This is due to the salinity of the pericardial fluid which has an impedance of approximately one-fourth that of the myocardium itself. In the alternative, verification of complete needle puncture can be verified by means of radio-opaque dye injection, as observed under fluoroscopy.

Figure 4A:
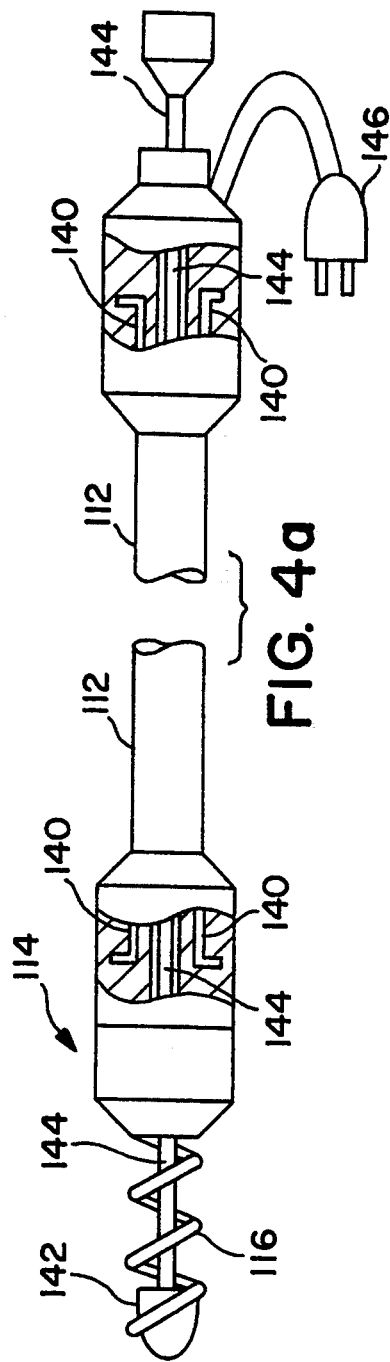

Lead 12 as illustrated in FIGS. 1 and 2 may be transvenously introduced by means of the counter-rotation technique typically used in conjunction with fixed screw endocardial pacing leads. However, in alternative embodiments, the lead may be provided with means for preventing snagging or catching of the coiled needle at undesired places along the introduction path. In addition, some provision may be made for enhancing the physician's ability to impart a twisting motion to coiled needle in order to screw it in to the myocardial tissue. FIGS. 4a–4c illustrates such alternative embodiments.

FIG. 4a shows a partially exploded lead 112 and sensor/needle assembly 110 is provided with reinforcing stylets 140 molded into lead body 112. Stylets 140 are made of wire or the like, and serve to provide rigidity along the length of lead 112 such that a torquing force applied at the proximal end of lead 112 will needle 16 at the distal end of lead 112 to be screwed into myocardial tissue. In addition, a silicone rubber stopper 142 is disposed within the coils of needle 116, and is initially in an extending position as shown in FIG. 4a. Stopper 142 is releasably attached to a stylet 144 which extends along the length of lead 112 and through a lumen through sensor 114. Stopper 142, in the extended position of FIG. 4a, protects needle tip 116' from catching or snagging during the lead introduction procedure. Electrical connector 148 serves to couple sensor 114 to an implantable medical device such as a pacemaker.

Referring now to FIG. 4b, when lead 112 has been introduced into the patient and the distal end thereof is brought into contact with myocardial tissue 36, stopper 142 is retracted by pulling, in the direction of arrow 146, on the proximal end of stylet 144. In this way, stopper 144 is pulled toward the base of coiled needle 116, where it will not interfere with the screwing in of needle 116.

Finally, as shown in FIG. 4c, coiled needle 116 is screwed into place by twisting or torquing the proximal end of lead 112, as indicated by arrow 148, allowing needle tip 116' to fully penetrate myocardial tissue 136. Also shown in FIG. 4c is one means by which needle 16 may be back-filled with blood during the implant procedure in order to eliminate the possibility of an embolism resulting from air trapped in hollow needle 116. In particular, a lumen in lead 112 may allow a syringe to be coupled to needle 116, thereby allowing the physician to draw blood into needle 116 during introduction of lead 112. In this embodiment, a valve means must be provided to seal needle 116 from the lumen after implant so that pressure may be efficiently communicated to the sensor 114.

Figure 5:
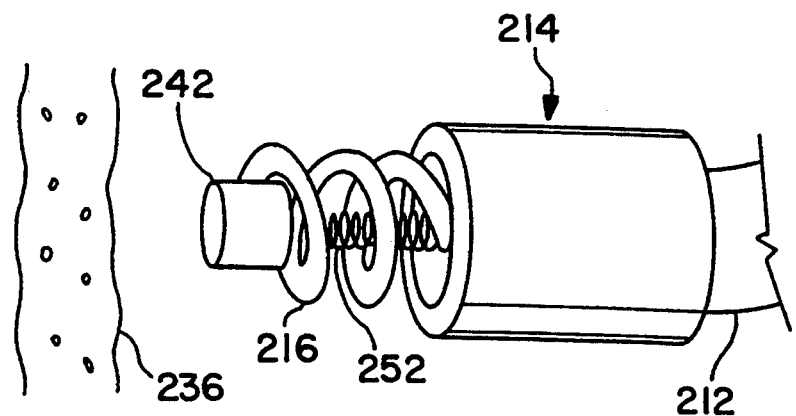
FIG. 5 is an illustration of a lead and pressure sensor assembly in accordance with an additional alternative embodiment of the invention.

FIG. 5 illustrates a variation on the needle-protecting stopper arrangement described with reference to FIGS. 4a, 4b, and 4c. In the alternative embodiment of FIG. 5, a stopper 242 is disposed within the coils of needle 216 in a manner similar that of stopper 242 from FIG. 4a. In FIG. 5, however, stopper 242 is held in an extending position by means of a spring 252. As lead 212 is introduced, stopper 242 protects tip 216' of needle 216. When the distal end of lead 212 is brought into contact with myocardial tissue 236, spring 252 is compressed within the coils of needle 216, allowing needle tip 216' to enter tissue 236.

Figure 6:
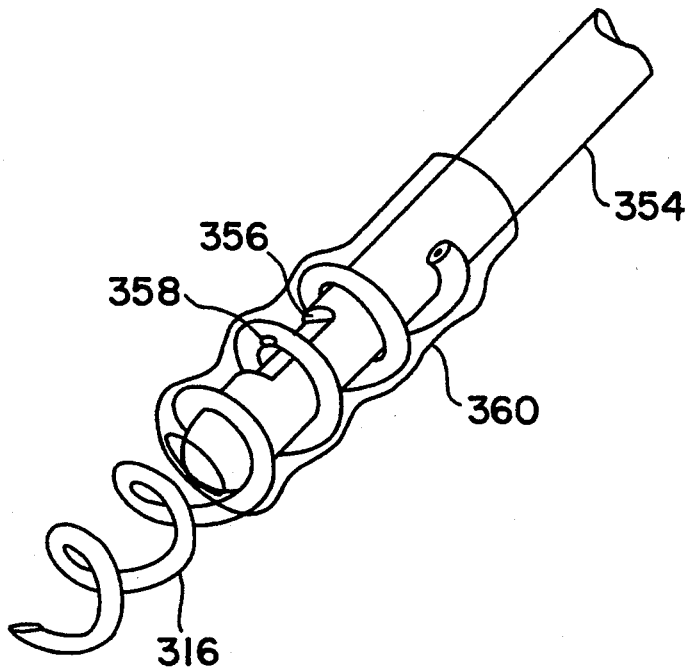
FIG. 6 is an illustration of a lead and pressure sensor assembly in accordance with an additional alternative embodiment of the invention.

FIG. 6 illustrates an additional alternative embodiment of a hollow needle pressure sensor lead in accordance with the present invention. In FIG. 6, a standard, commercially available pressure sensor catheter 354 is modified to become a coiled needle type sensor in accordance with the present invention. Pressure-sensing catheter 354 as illustrated is the well-known and commercially available Millar catheter, manufactured by Millar Instruments, Inc., 6001 Gulf Freeway, Houston, Tex., 77023.

The Millar catheter has a pressure-sensor port 356 disposed near its distal end. In adapting the Millar catheter in accordance with the present invention, a coiled, hollow needle 316 is disposed around and partially coextensive with the distal end of catheter 354. Needle 316 is identical to needle 16 shown in FIG. 1, except that needle 316 is provided with a hole 358 located to provide access to pressure sensor port 356 in catheter 354. Needle 316 is secured to the distal end of catheter 354 by means of shrink-fit silicone tubing 360.

Figure 7:
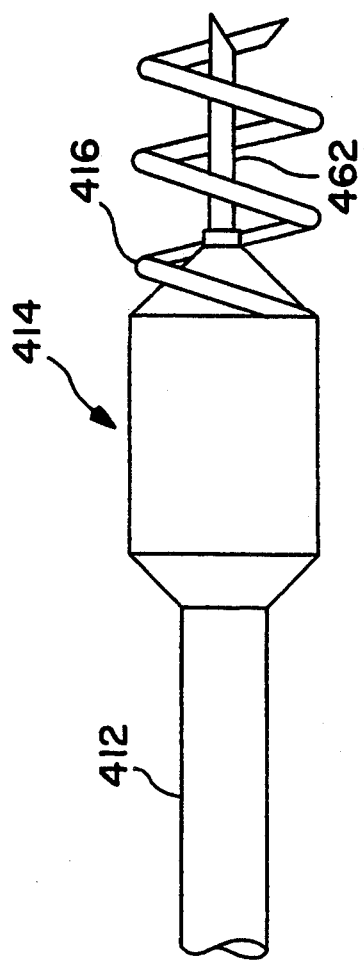
FIG. 7 is an illustration of a lead and pressure sensor assembly in accordance with an additional alternative embodiment of the present invention.

In the alternative embodiment of FIG. 7, lead 412 and sensor 414 correspond generally to lead 12 and sensor 14 of FIG. 1. However, in the embodiment of FIG. 7, a solid coiled needle 416, rather than a hollow coiled needle, is used. A straight, hollow needle or tube 462 extending along the central axis of coiled needle 416 is provided to communicate pressure gradients to sensor 414. In operation, coiled needle 416 provides the means for screwing the lead into myocardial tissue.

Figure 8:
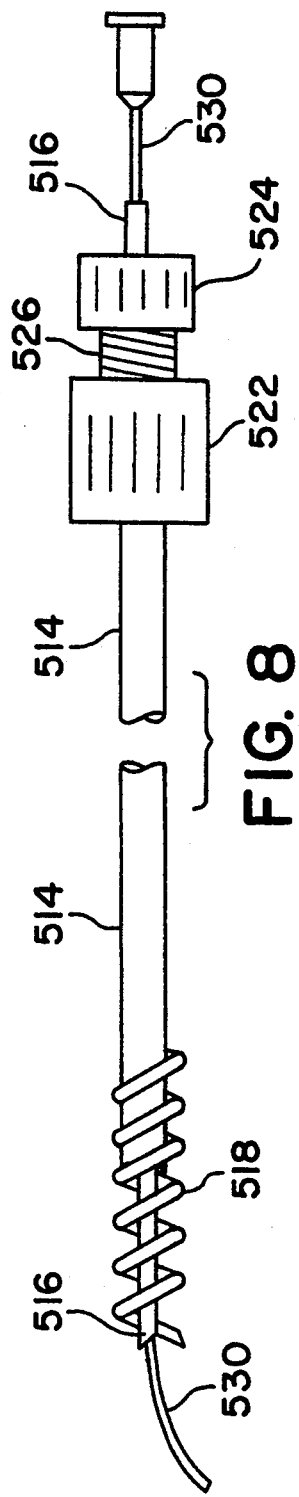
FIG. 8 is an illustration of a lead and pressure sensor assembly in accordance with embodiment an additional alternative of the present invention.

FIG. 8 illustrates yet another alternative embodiment of the present invention. In this embodiment, the lead body 512 takes the form of a hollow torque cable 514 which may comprise two or more counter-wound metal coils with a central lumen therethrough. The exterior of the lead body is provided with an insulative coating or sheath. Alternatively, the lead body may comprise only a single coil, mounted within a plastic sheath or may comprise any of the numerous torque-transferring tubular structures employed in modern diagnostic and therapeutic catheters. Extending from the interior of the torque cable is a 23 gauge needle 516, which is movably located within the lumen within the torque cable 514 and extends through the proximal end of the torque cable. The exterior surface of needle 516 may also be provided with an insulating coating. Mounted around the exterior of the distal end of the torque cable is a solid, coiled needle 518, which is rotated into the cardiac tissue by corresponding rotation of the proximal end of the torque cable 514. Extending through the interior of the needle 516 and out the distal end thereof is a small diameter tube 530 fabricated of polyamide or other flexible plastic, which serves as a pressure conduit which may be coupled to an external pressure transducer by means of luer fitting 532, in the fashion of presently available manometer type pressure sensing catheters.

To implant the lead, it is first advanced to the desired site by means of a guide catheter. The proximal end of the torque cable 514 is provided with a handle 522 which is initially used to rotate the torque cable to screw coiled needle 518 into the tissue. The distal end of needle 516 is then advanced out the distal end of the torque cable 514 by rotation of handle 524, which screws into handle 520. The pitch of the threads 526 of handle 524 and the corresponding pitch of threads internal to handle 520 should be extremely fine, so that the needle 516 is advanced very slowly. In order to measure the point at which the needle 518 enters the pericardial space, the impedance between the needle and a ground electrode may be monitored. The point at which the needle 516 enters the pericardial fluid will be marked by a abrupt, significant change in impedance (30% or more). At this point, tube 530 may be advanced into the pericardial space for pressure measurements. The extreme flexibility of tube 530 will prevent it from perforating the pericardium.

Although specific embodiments of the invention have been disclosed in detail, this has been done for the purposes of illustration only, and has not been intended to be limiting with respect to the scope of the present invention. Therefore, the illustrated embodiments should be considered exemplary, rather than limiting with regard to the scope of the following claims.

What is claimed is:

1. A pressure sensor lead comprising:
   an elongated implantable lead body having proximal and distal ends and having at least one electrical conductor wire therein extending between said proximal and distal ends;
   a pressure sensor means for generating an electrical output signal corresponding to pressure applied thereto, said pressure sensor means being disposed near said distal end of said lead and coupled to said at least one electrical conductor wire;
   a tissue piercing hollow needle having a base and a tip and an internal lumen, mounted to said pressure sensor means such that lumen serves as means to communicate pressure to said pressure sensor means, wherein said needle is electrically conductive and is electrically coupled to said at least one electrical conductor wire.

2. A pressure sensor lead in accordance with claim 1, wherein said lumen is filled with a pressure-conducting medium.

3. A pressure sensor lead in accordance with claim 2, wherein said pressure-conducting medium is silicone rubber.

4. A pressure sensor lead in accordance with claim 2, wherein said pressure-conducting medium is a non-compressible liquid.

5. A pressure sensor lead in accordance with claim 4, wherein said medium is a saline solution.

6. A pressure sensor lead in accordance with claim 4, wherein said medium is fluid silicone.

7. A pressure sensor lead in accordance with claim 1, wherein a hole is provided in said hollow needle at a point between said base and said tip.

8. A pressure sensor lead according to claim 1 wherein said sensor means comprises a conductive housing and wherein said housing is coupled to said at least one electrical conductor wire.

9. A pressure sensor lead according to claim 1 wherein said at least one conductor wire comprises two mutually insulated electrical conductors.

10. A pressure sensor lead according to claim 1 further comprising a solid, coiled needle mounted to the said pressure sensor means.

11. A pressure sensor lead comprising:
   an elongated implantable lead body having proximal and distal ends and having an electrical conductor therein extending between said proximal and distal ends;
   a pressure sensor means for generating an electrical output signal corresponding to pressure applied thereto, said pressure sensor means being disposed near said distal end of said lead and coupled to said electrical conductor;
   a hollow needle having a base and a tip and an internal lumen, mounted to said pressure sensor means such that lumen serves as means to communicate pressure to said pressure sensor means, wherein said hollow needle is a coiled needle.

12. A pressure sensor lead in accordance with claim 11, further comprising a stopper retractably disposed within said coiled needle.

13. A pressure sensor lead in accordance with claim 12, further comprising a spring, coupling said stopper to said pressure sensor means.

14. A pressure sensing lead, comprising:
   an elongated implantable lead body having proximal and distal ends;
   a pressure sensor means for sensing pressure adjacent the distal end of said lead body, said pressure sensor means comprising a hollow needle extendable from the distal end of said lead;
   a coiled needle, mounted to said distal end of said lead body, around said hollow needle.

15. A pressure sensing lead according to claim 14, further comprising means for screwing said coiled needle into body tissue.

16. A pressure sensing lead according to claim 15, further comprising means for advancing said hollow needle into said body tissue after screwing said coiled needle into body tissue.

17. A pressure sensing lead according to claim 16 further comprising a flexible tube extending through said elongated lead body and advanceable through said hollow needle.

* * * * *